US 8,985,852 B2

(12) United States Patent
Theiss

(10) Patent No.: US 8,985,852 B2
(45) Date of Patent: Mar. 24, 2015

(54) MONITORING DEVICE FOR A CT SCANNER GANTRY

(75) Inventor: Klaus Theiss, Gilching (DE)

(73) Assignee: Schleifring Und Apparatebau GMBH (DE)

( * ) Notice: Subject to any disclaimer, the term of this patent is extended or adjusted under 35 U.S.C. 154(b) by 287 days.

(21) Appl. No.: 13/547,725

(22) Filed: Jul. 12, 2012

(65) Prior Publication Data

US 2014/0016758 A1    Jan. 16, 2014

(51) Int. Cl.
  *H05G 1/02* (2006.01)
  *A61B 6/00* (2006.01)
  *A61B 6/03* (2006.01)

(52) U.S. Cl.
  CPC .............. *A61B 6/4447* (2013.01); *A61B 6/035* (2013.01)
  USPC ........................................................ 378/197

(58) Field of Classification Search
  USPC .............................. 378/197, 196, 205, 207, 15
  See application file for complete search history.

(56) References Cited

U.S. PATENT DOCUMENTS

| 5,631,944 A * | 5/1997 | Kimura et al. ................. 378/134 |
| 6,097,030 A | 8/2000 | Tokarski et al. |
| 6,301,324 B1 | 10/2001 | Pearson, Jr. et al. |
| 6,580,777 B1 * | 6/2003 | Ueki et al. ...................... 378/17 |
| 8,089,621 B2 * | 1/2012 | Horio ............................ 356/139 |

\* cited by examiner

*Primary Examiner* — Irakli Kiknadze
(74) *Attorney, Agent, or Firm* — Yakov Sidorin; Quarles & Brady LLP

(57) ABSTRACT

A CT scanner gantry comprises a base with a tiltable frame holding a rotating part, the rotating part having a rotation axis and drive means for tilting the tiltable frame with respect to the base. Furthermore, a tilt drive control unit is provided to control the drive means. In inclination sensor is provided at the tiltable frame to indicate the inclination of the tiltable frame with respect to the center of gravity of earth to the tilt drive control unit.

7 Claims, 2 Drawing Sheets

MONITORING DEVICE FOR A CT SCANNER GANTRY

TECHNICAL FIELD

The invention relates to an X-ray computed tomography (CT) scanner, and, more particularly, to a device for monitoring specific characteristic parameters of a gantry of a CT scanner.

BACKGROUND ART

A conventional X-ray CT scanner has a gantry holding an X-ray tube and a detector. The gantry has a stationary part which is standing at or mounted to the floor of a hospital room. Furthermore, it has a rotating part held by a bearing at the stationary part. The rotating part holds the X-ray tube and the X-ray detector at opposing positions, and allows rotation thereof around a patient table on which a patient may be positioned. For specific types of imaging, at least the rotating part of the gantry may be tilted against parts of the stationary part and against the patient table.

A general CT scanner is disclosed in the U.S. Pat. No. 6,301,324. A tiltable rotating part of a gantry is disclosed in the U.S. Pat. No. 6,097,030. Here a detector position sensor, such as a decoder is coupled to a tilt drive servo motor and configured to generate signals representative of the detector tilt angle. The drawback of this embodiment is a very complex decoder and the requirement of a position reference of detector tilt. Furthermore a decoder calibration may be required when powering on the CT scanner. A decoder has to be mounted and aligned. A relative decoder requires a zero position search after power on and thus a disadvantageous movement of the tilt gantry. A decoder as disclosed in U.S. Pat. No. 6,097,030 is often called encoder or rotary encoder.

SUMMARY OF THE INVENTION

The embodiments are configured to ensure simplified monitoring of mechanical states of the gantry, the states including at least the tilting angle of the rotating part of the gantry.

In an embodiment, a CT scanner gantry has a base which is stationary and preferably is located at or even fixed to the floor of a hospital room. This base holds a tiltable frame which may be tilted against the base. A rotating part for holding an X-ray tube and an X-ray detector is mounted at the tiltable frame. An inclination sensor is provided at the tiltable frame to determine the angle of a vector at a right angle to the rotation axis of the rotating part with respect to the center of gravity of the earth. Therefore, the angle between the rotation axis of the rotating part and the center of gravity of earth or any other measure relating to this angle may be determined by the inclination sensor. This allows for a very precise adjustment of the rotation axis of the CT scanner with respect to the patient table and offers an excellent long-term stability.

Preferably, the tiltable frame is tilted by drive means which may be a lifting spindle mounted between the base and the tiltable frame to generate a torque. There may be two lifting spindles in parallel, being located at different sides of the rotating part at the tiltable frame. The lifting spindles preferably are driven by a spindle drive which may be an electric motor together with a gear. Generally it is preferred, if the lifting spindle has a comparatively low pitch which allows for precise adjustment and makes the spindle self-locking. To determine the tilting angle, the angular position of the lifting spindle or any device related thereto, such as the motor, is measured. This is also the case in the prior art cited above. Most common for angular measurement is a relative position encoder which requires at least one further reference position encoder to determine the absolute tilting angle of the rotating part. Standard absolute angle encoders cannot be used, as the lifting spindle requires a plurality of turns for moving between the lowest possible and the highest possible tilting angle. By using a relative position encoder, usually when turning on the power of the CT apparatus, a calibration run must be performed, therefore driving the tiltable frame to the absolute position reference. When this has been done, the relative angle position encoder may be used to determine the position of the lifting spindle with respect to the absolute position reference. A calibration run is time-consuming and requires moving of the comparatively heavy and large tiltable frame of the gantry. Furthermore, a calibration run may result in a movement of the gantry prior to usage without initiation by operator and thus is unwanted. Such a calibration run is no more required when using the inclination sensor.

Although mechanical parts like the lifting spindle can be made comparatively stiff, there is some long-term deviation of the lifting spindle or by further connecting parts, connecting the lifting spindle to the base or to the tiltable frame. Such deviations may be caused by thermal expansion due to large operating temperature changes within the CT scanner gantry or by wear of the lifting spindle or any other part. The long-term stability of these mechanical components was sufficient for previous generations of CT scanners. With increasing resolution of the CT scanners, the requirements to precision of the tilting components are increasing. As the inclination sensor is substantially independent of any further mechanical components in the tiltable mechanism, and therefore delivers the best possible long-term stability which is suitable for future higher precision and resolution tomography scanners.

As the inclination sensor is independent of the lifting spindle, alternative tilting drive systems may be used. For example, tilt may be performed by a hydraulic system or gear wheels or worm gear.

As the inclination sensor is very sensitive, it may be used for detecting vibrations or oscillations in the tiltable frame or the rotating part. Preferably, a high pass filter is used to filter higher frequency components from the inclination sensor. Preferably, the lower cut-off frequency of the high pass filter is in the order of magnitude or below the rotational frequency of the rotating part of the gantry. For example, if the rotating part rotates with two revolutions per second, the cut-off frequency of the low pass filter is below 2 Hz, preferably below 1 Hz. It is further preferred that the cut-off frequency of the low pass filter is above the frequency of movement of the tilting drive which may be on the order of magnitude of 0.1 Hz. By using such a low pass filter or by integrating an acceleration sensor, oscillations or vibrations which occur once per revolution may easily be detected. If the amplitude or the level of such vibrations or oscillations exceeds a threshold value, a warning may be generated. Furthermore, the oscillations or vibrations may be continuously displayed. Furthermore, a quality value may be calculated for the measured amplitudes. Generally, a CT scanner running with lower amplitudes is of a better quality than a CT scanner running with higher amplitudes. The amplitudes will increase, for example, with extended time of operation of the CT scanner, when for example the bearing holding the rotating part within the tiltable frame gets worn, or other drive parts like the drive belt or drive motor. Upon detection of vibrations or oscillations, preferably above a certain threshold level, the CT scanner may be shut down, or at least the rotation of the rotating part may be stopped. Furthermore an error message may be generated. In a further embodiment, a profile of the oscillation amplitude as a function of rotational speed may be measured and used to choose optimal operational speed ranges with low oscillations.

In another embodiment a spectral analysis of the frequency spectrum of the signals of the inclination sensor may be done to evaluate the state of the CT scanner gantry. Signals at unexpected frequencies or moving frequencies of signals may indicate an approaching failure.

In a further embodiment, the inclination sensor may measure inclination with respect to a second axis being at a right angle to the first axis. This allows further detection of failures or wear of the CT scanner.

In another embodiment two inclination sensors are provided. One sensor is located at each side of the rotating part. This allows for consistency checking and for determining torsion of the tiltable frame.

In another embodiment, it is preferred, if the inclination sensor has a digital bus system for connection with a tilt control unit. It is further preferred, if the evaluation of at least one of the values generated by the inclination sensor is done by a drive inverter for driving the tilt drive motor or a controller external to the tilt drive motor or drive inverter.

The inclination sensor may be any sensor using a mass which is influenced by the earth gravity and which further has means for detecting the position or the angle of the mass. Preferably, the inclination sensor comprises a microelectromechanical system. In an alternative embodiment, the sensor could be based on the measurement of thermal air movements inside the sensor housing.

BRIEF DESCRIPTION OF THE DRAWINGS

In the following, the invention will be described by way of example, without limitation of the general inventive concept, on examples of embodiment and with reference to the drawings.

Figure 1:
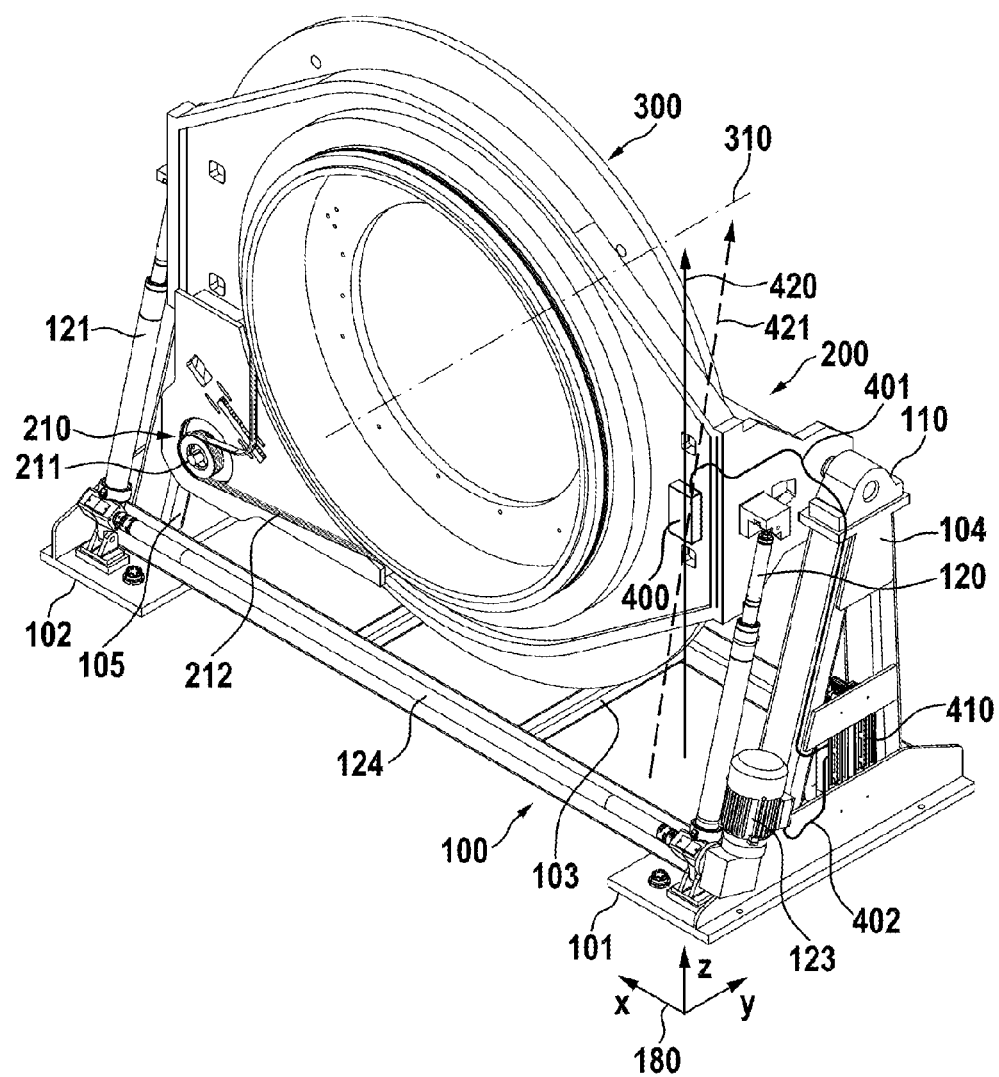
FIG. 1 shows a tiltable gantry of a CT scanner.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

In FIG. 1, a tiltable gantry is shown. A base 100 preferably has at least one support base 101, 102, which most preferably is fixed e.g. by screws or bolts to a supporting ground, which may be the floor of a hospital room. Preferably, the support structure 103 is provided to connect the support bases 101, 102 to a solid base. Furthermore, at least one strut 104, 105 is provided. In this embodiment, a first strut 104 is attached to first support base 101, while a second strut 105 is attached to second support base 102. Bearings 110 are mounted on top of the struts 104, 105 to hold the tiltable frame 200. The tiltable frame 200 holds the rotating part 300, having a rotation axis 310. On each side of the rotating part, the tiltable frame is held by one of the struts 104, 105. For rotating the rotating part, a drive system is provided. It preferably comprises of an electrical motor 210, having at least one pulley 211 for driving a belt 212, which further drives the rotating part 300. It may also comprise a direct drive which may be a motor integrated into the bearing. For tilting the tiltable frame 200, at least one lifting spindle 120, 121 is provided. In this embodiment, two lifting spindles are provided, whereas a lifting spindle is mounted close to each strut. The lifting spindles are driven by lifting spindle drive motor 123. While the first lifting spindle is directly mounted to the motor 123, the second lifting spindle 121 is driven by means of drive shaft 124. The inclination sensor 400 is mounted to the tiltable frame. It is preferably mounted to a plane being under a right angle to the rotation axis of the rotating part. It is connected by a first cable 401 to a tilt drive control unit 410. This control unit further may control lifting spindle drive motor 123 by means of a second cable 402.

A main axis 420 of the inclination sensor 400 is under a right angle to the rotation axis 310 of the rotating part 300. When there is no tilt, the main axis 420 is parallel to the z-axis of the main coordinate system 180, having an x-axis parallel to the front of the CT scanner gantry, a y-axis parallel to the untilted rotation axis of the CT scanner 310, and a z-axis under a right angle to the center of gravity of earth.

When tilting the tiltable frame, the main axis 420 gets tilted as shown with tilted axis 421. This tilt is measured by the inclination sensor 400.

It is preferred, if the inclination sensor has at least a second sensor axis and therefore can detect inclination relative to a second axis, preferably at a right angle to the first axis. Such a second axis may be used for adjustment of the horizontal alignment of the gantry, specifically when installing the gantry. It may be used at any later time to verify correct alignment of the gantry. Furthermore it may be useful when installing the gantry to have the tiltable frame 200 locked into a position relative to the base 100. Then the inclination sensor 400 may be used to verify complete alignment of the gantry. This may specifically be useful, when a CT scanner is used in a mobile application like within a container or a truck.

In FIG. 1, a tiltable gantry is shown. A base 100 preferably has at least one support base 101, 102, which most preferably is fixed e.g. by screws or bolts to a supporting ground, which may be the floor of a hospital room. Preferably, the support structure 103 is provided to connect the support bases 101, 102 to a solid base. Furthermore, at least one strut 104, 105 is provided. In this embodiment, a first strut 104 is attached to first support base 101, while a second strut 105 is attached to second support base 102. Bearings 110 are mounted on top of the struts 104, 105 to hold the tiltable frame 200. The tiltable frame 200 holds the rotating part 300, having a rotation axis 310. On each side of the rotating part, the tiltable frame is held by one of the struts 104, 105. For rotating the rotating part, a drive system is provided. It preferably comprises of an electrical motor 210, having at least one pulley 211 for driving a belt 212, which further drives the rotating part 300. It may also comprise a direct drive which may be a motor integrated into the bearing. For tilting the tiltable frame 200, at least one lifting spindle 120, 121 is provided. In this embodiment, two lifting spindles are provided, whereas a lifting spindle is mounted close to each strut. The lifting spindles are driven by lifting spindle drive motor 123. While the first lifting spindle is directly mounted to the motor 123, the second lifting spindle 121 is driven by means of drive shaft 124. The inclination sensor 400 is mounted to the tiltable frame. It is preferably mounted to a plane that is at a right angle to the rotation axis of the rotating part. It is connected by a first cable 401 to a tilt drive control unit 410. This control unit further may control lifting spindle drive motor 123 by means of a second cable 402.

Figure 2:
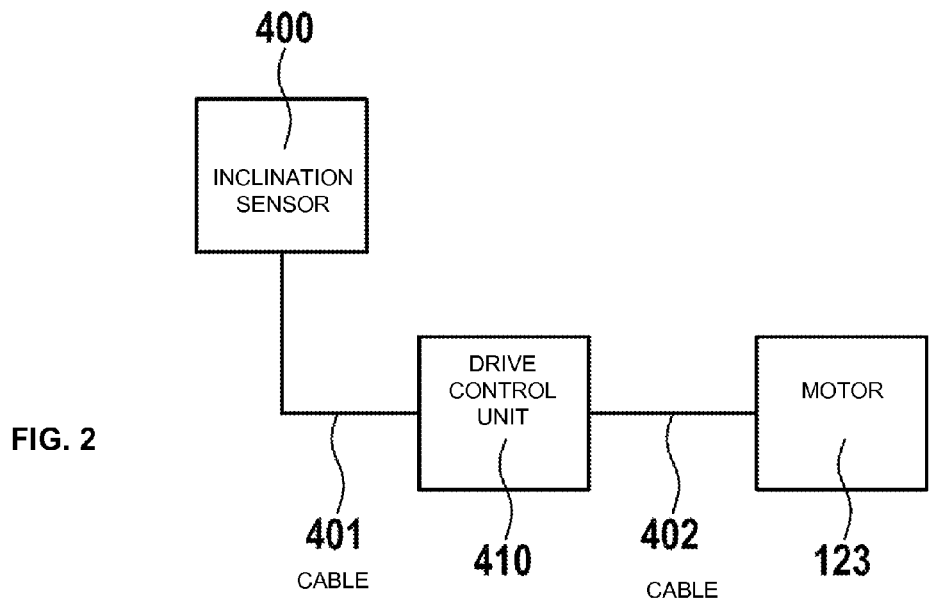
FIG. 2 shows a block diagram of the tilt control.

In FIG. 2, a schematic diagram of the tilt drive system is shown. Tilt drive control unit 410 receives an inclination signal from the inclination sensor 400 via cable 401. According to the signals measured by inclination sensor 400, the lifting spindle drive motor 123 is controlled via cable 402 to adjust the position of the tiltable frame according to a set point value which may be generated by a CT scanner control unit. In a specific case, the tilt drive control unit may be arranged as part of any other control unit like a motor control unit or a CT scanner control unit.

The inclination sensor may also help to simplify the initial adjustment of the CT scanner gantry during installation, as it may indicate an undesired or wrong positioning which would require additional support or adjustment of the support bases. This may be further supported by a third axis of the inclination sensor.

It is preferred that the inclination sensor has at least a second sensor axis and therefore can detect inclination relative to a second axis, preferably at a right angle to the first axis. Such a second axis may be used for adjustment of the horizontal alignment of the gantry, specifically when installing the gantry. It may be used at any later time to verify correct alignment of the gantry. Furthermore it may be useful when installing the gantry to have the tiltable frame 200 locked into a position relative to the base 100. Then the inclination sensor 400 may be used to verify complete alignment of the gantry. This may specifically be useful, when a CT scanner is used in a mobile application like within a container or a truck.

Figure 3:
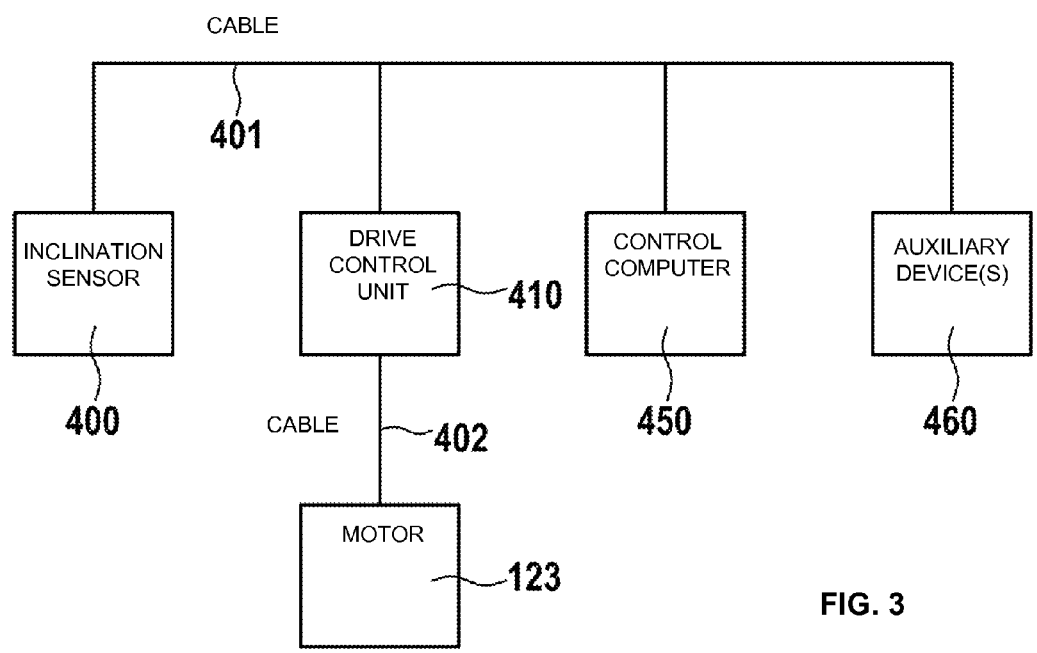
FIG. 3 shows the inclination sensor connected by means of a digital bus.

In FIG. 3, an inclination sensor 400 is connected by a digital bus 401 to other devices like drive control unit 410, a control computer 450 and optionally to other devices 460, such as further sensors or computers. Preferably the digital bus is a CAN (controller area network) or any other suitable bus system.

Further embodiment of the invention relates to a method for tilting a CT scanner gantry, the method comprising the steps of reading the inclination value of an inclination sensor which preferably indicates the inclination of a tiltable frame of the gantry with respect to the center of gravity of earth.

It will be appreciated by those skilled in the art and having the benefit of this disclosure that this invention is believed to provide a CT scanner gantry. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A CT scanner gantry comprising
a base with a tiltable frame holding a rotating part, the rotating part having a rotation axis,
drive means for tilting the tiltable frame with respect to the base, and
a tilt drive control unit to control the drive means,
characterized in that
an inclination sensor is provided at the tiltable frame to indicate the inclination of the tiltable frame with respect to the center of gravity of earth to the tilt drive control unit, and
a high pass filter is provided to filter the measurement signals from the inclination sensor.

2. The CT scanner gantry according to claim 1, characterized in that the inclination sensor has a main axis at a right angle to the rotation axis of the rotating part.

3. The CT scanner gantry according to claim 1, characterized in that the inclination sensor is configured to measure inclination of a second axis that is at a right angle to the main axis.

4. The CT scanner gantry according to claim 1, characterized in that the tilt drive control unit compares the signal of the high pass filter with a threshold value to indicate a failure in the CT scanner gantry.

5. The CT scanner gantry according to claim 1, characterized in that the tilt drive control unit is configured to compare a filtered signal of the inclination sensor with a threshold value and, when said filtered signal exceeds the threshold value,
to effectuate at least one of i) stopping of a tilting motion of the tiltable frame with respect to the base, and ii) shutting down the CT scan gantry.

6. The CT scanner gantry according to claim 1, characterized in that the tilt drive control unit is configured to compare a signal generated by the inclination sensor with a threshold value and, when said filtered signal exceeds the threshold value, to effectuate at least one of i) stopping of a tilting motion of the tiltable frame with respect to the base, and ii) shutting down the CT scan gantry.

7. The CT scanner gantry according to claim 1, characterized in that means is provided for locking the tiltable frame into a fixed position relative to the base to allow at least one of (i) alignment of the base, and (ii) leveling of the base.

* * * * *